United States Patent
Kanaoka et al.

(10) Patent No.: US 9,192,418 B2
(45) Date of Patent: Nov. 24, 2015

(54) LASER PROCESSING APPARATUS, OSSEOINTEGRATION METHOD, IMPLANT MATERIAL, AND IMPLANT-MATERIAL FABRICATION METHOD

(75) Inventors: Masaru Kanaoka, Tokyo (JP); Taira Ogita, Tokyo (JP); Tooru Murai, Tokyo (JP); Shigeru Tadano, Hokkaido (JP); Masahiro Todoh, Hokkaido (JP)

(73) Assignees: NATIONAL UNIVERSITY CORPORATION HOKKAIDO UNIVERSITY, Sapporo-shi (JP); Mitsubishi Electric Corporation, Tokyo (JP)

( * ) Notice: Subject to any disclaimer, the term of this patent is extended or adjusted under 35 U.S.C. 154(b) by 1823 days.

(21) Appl. No.: 12/438,264

(22) PCT Filed: Aug. 21, 2007

(86) PCT No.: PCT/JP2007/066203
§ 371 (c)(1),
(2), (4) Date: Apr. 9, 2009

(87) PCT Pub. No.: WO2008/023708
PCT Pub. Date: Feb. 28, 2008

(65) Prior Publication Data
US 2010/0049179 A1 Feb. 25, 2010

(30) Foreign Application Priority Data

Aug. 22, 2006 (JP) ................... 2006-225329
Feb. 20, 2007 (JP) ................... 2007-039878

(51) Int. Cl.
*A61B 18/18* (2006.01)
*A61N 5/06* (2006.01)
(Continued)

(52) U.S. Cl.
CPC ............... *A61B 17/88* (2013.01); *A61B 18/20* (2013.01); *A61C 1/0046* (2013.01);
(Continued)

(58) Field of Classification Search
CPC .............. A61B 18/20; A61B 18/22; A61B 2018/00636; A61F 2/30; A61F 2/4601; A61F 2/4644; A61F 2002/0086
USPC .................. 433/224; 607/88–94; 606/11
See application file for complete search history.

(56) References Cited

U.S. PATENT DOCUMENTS 4,542,539 A    9/1985 Rowe, Jr. et al.
5,071,436 A *  12/1991 Huc et al. ............. 424/423
(Continued)

FOREIGN PATENT DOCUMENTS

EP    0 865 766 A2    9/1998
EP    1 358 852 A1   11/2003
(Continued)

OTHER PUBLICATIONS

European Search Report dated Sep. 19, 2012 issued in a corresponding European Patent Application No. 12177603.3.
(Continued)

*Primary Examiner* — Lynsey Crandall
*Assistant Examiner* — Sebastian X Lukjan
(74) *Attorney, Agent, or Firm* — Sughrue Mion, PLLC; Richard C. Turner

(57) ABSTRACT

A method of integrating bone and implant material includes drilling a hole in either one of the bone and the implant material through to a junction of the bone and the implant material by applying a laser beam to either one of the bone and the implant material and integrating the bone and the implant material by applying a laser beam to the junction through the hole drilled at the drilling.

8 Claims, 10 Drawing Sheets

(51) Int. Cl.

| | | |
|---|---|---|
| *A61C 5/02* | (2006.01) | |
| *A61B 17/88* | (2006.01) | |
| *A61B 18/20* | (2006.01) | |
| *A61C 1/00* | (2006.01) | |
| *A61C 8/00* | (2006.01) | |
| *B23K 26/00* | (2014.01) | |
| *B23K 26/32* | (2014.01) | |
| *B23K 26/38* | (2014.01) | |
| *B23K 26/40* | (2014.01) | |
| *B29C 65/16* | (2006.01) | |
| *B29C 65/82* | (2006.01) | |
| *B29C 65/00* | (2006.01) | |
| *A61F 2/46* | (2006.01) | |
| *A61F 2/30* | (2006.01) | |
| *A61B 18/22* | (2006.01) | |
| *A61F 2/00* | (2006.01) | |
| *A61B 18/00* | (2006.01) | |
| *A61B 17/16* | (2006.01) | |
| *A61B 17/00* | (2006.01) | |

(52) U.S. Cl.
CPC .......... *A61C 8/0089* (2013.01); *B23K 26/0009* (2013.01); *B23K 26/0036* (2013.01); *B23K 26/0045* (2013.01); *B23K 26/0081* (2013.01); *B23K 26/3206* (2013.01); *B23K 26/3273* (2013.01); *B23K 26/385* (2013.01); *B23K 26/403* (2013.01); *B29C 65/16* (2013.01); *B29C 65/8253* (2013.01); *B29C 66/7483* (2013.01); *A61B 17/16* (2013.01); *A61B 17/164* (2013.01); *A61B 18/22* (2013.01); *A61B 2017/00508* (2013.01); *A61B 2018/00565* (2013.01); *A61B 2018/00601* (2013.01); *A61B 2018/00619* (2013.01); *A61B 2018/00636* (2013.01); *A61B 2018/00779* (2013.01); *A61F 2/30* (2013.01); *A61F 2/4601* (2013.01); *A61F 2/4644* (2013.01); *A61F 2002/0086* (2013.01); *B29C 65/1616* (2013.01); *B29C 65/1619* (2013.01); *B29C 65/1648* (2013.01); *B29C 65/1651* (2013.01)

(56) References Cited

U.S. PATENT DOCUMENTS

| | | | |
|---|---|---|---|
| 5,092,773 A * | 3/1992 | Levy | 433/224 |
| 5,776,193 A | 7/1998 | Kwan et al. | |
| 5,993,456 A | 11/1999 | Speitling et al. | |
| 6,086,367 A * | 7/2000 | Levy | 433/29 |
| 6,187,047 B1 | 2/2001 | Kwan et al. | |
| 6,231,567 B1 | 5/2001 | Rizoiu et al. | |
| 2002/0001608 A1 * | 1/2002 | Polson et al. | 424/426 |
| 2003/0003127 A1 | 1/2003 | Brown et al. | |
| 2003/0004578 A1 | 1/2003 | Brown et al. | |
| 2003/0153981 A1 | 8/2003 | Wang et al. | |
| 2004/0204647 A1 * | 10/2004 | Grupp et al. | 600/431 |
| 2004/0249370 A1 | 12/2004 | Berna et al. | |
| 2005/0096655 A1 | 5/2005 | Trinchese | |
| 2005/0100578 A1 | 5/2005 | Schmid et al. | |

FOREIGN PATENT DOCUMENTS

| | | |
|---|---|---|
| EP | 1 477 126 A1 | 11/2004 |
| JP | 62-502170 A | 8/1987 |
| JP | 64-037475 A | 2/1989 |
| JP | 64-052471 A | 2/1989 |
| JP | 02-504478 A | 12/1990 |
| JP | 04-053550 A | 2/1992 |
| JP | 04-300535 A | 10/1992 |
| JP | 06-007425 A | 1/1994 |
| JP | 07-051278 A | 2/1995 |
| JP | 2000-302622 A | 10/2000 |
| JP | 2002-301091 A | 10/2002 |
| JP | 2003-102755 A | 4/2003 |
| JP | 2003-126237 A | 5/2003 |
| JP | 2003-169845 A | 6/2003 |
| JP | 2005/512702 A | 5/2005 |
| WO | 86/03958 A1 | 7/1986 |
| WO | 89/08432 A1 | 9/1989 |
| WO | 02/17820 A1 | 3/2002 |
| WO | 2005-047467 A2 | 5/2005 |

OTHER PUBLICATIONS

Supplementary Partial European Search Report dated Feb. 25, 2011.
European Search Report dated Apr. 29, 2013 issued in European Patent Application No. 13153435.6.
Japanese Office Action (Notice of Rejection) Jun. 25, 2013; Patent Application No. 2012 090896.
European Search Report dated Sep. 9, 2013 issued in European Patent Application No. 13153435.6.-1654/2596764.

* cited by examiner

FIG.2

| PROCESSING CONDITION | OUTPUT | 500 W | | | | | |
|---|---|---|---|---|---|---|---|
| | BEAM-ON TIME | 0.5 SEC | | | 1.0 SEC | | |
| | FOCAL POINT | 0 | 5 | 10 | 0 | 5 | 10 |
| | HOLE APPEARANCE (TOP SURFACE) | | | | | | |
| | HOLE DIAMETER | 0.619 mm | 0.978 mm | 1.259 mm | 0.444 mm | 0.790 mm | 1.528 mm |

| Ca | C | P | O | Na | Mg | Al | Si |
|---|---|---|---|---|---|---|---|
| 24.7% | 5.7% | 4.5% | 45.6% | - | 3.1% | 8.9% | 7.5% |

LASER PROCESSING APPARATUS, OSSEOINTEGRATION METHOD, IMPLANT MATERIAL, AND IMPLANT-MATERIAL FABRICATION METHOD

CROSS REFERENCE TO RELATED APPLICATION

This application is a National Stage of International Application No. PCT/JP2007/066203 filed Aug. 21, 2007, claiming priority based on Japanese Patent Application Nos. 2006-225329, filed Aug. 22, 2006 and 2007-039878, filed Feb. 20, 2007, the contents of all of which are incorporated herein by reference in their entirety.

TECHNICAL FIELD

The present invention relates to a laser processing apparatus that integrates bone and implant material, an osseointegration method, implant material, and an implant-material fabrication method.

BACKGROUND ART

Recently, a technology (e.g., a surgical apparatus) for integrating bone (bone tissue) and implant material made of biomedical material such as ceramics or composite material is being increasingly developed. When integrating the implant material and the bone, if even a slight change occurs in relative positions of the implant material and the bone during integration with each other, completion of the integration takes an extremely long time. Besides, if such a slight change is not detected and when the integration between the implant material and the bone is continued, the integration is finished while displacement is remained. Conventionally, to prevent occurrence of the slight change in the relative positions, a junction is fixed by a fixture that is rigid and heavy. Therefore, operation for integrating the implant material and the bone has been complicated and time-consuming.

Furthermore, to increase the strength of the integration between the implant material and the bone, the implant material and the bone are completely integrated with each other by using a metal bonding bolt, and thereafter, the bolt is removed. Accordingly, the integration between the implant material and the bone takes a long time, so that medical treatment for an affected area also takes a long time. Thus, a demand for integrating the bone and the implant material shortly and easily is growing.

Conventionally, to stabilize a relative position of implant material (surgical grafting material) to bone through promotion of bone bonding, the implant material is formed to have a textured surface so that bone tissue and the implant material can be integrated in a short time. For example, in an artificial hip composed of a femoral-sub-assembly to be fixed inside a femur of a patient and an acetabular-sub-assembly to be fixed inside an acetabulum of a patient, the femoral-sub-assembly includes an artificial stem having a textured surface or the like while the acetabular-sub-assembly includes an artificial cup having a textured surface or the like.

While the textured surface is formed to promote bone growth, because processes of (1) positioning, (2) immobilization with a cast, and (3) bone growth are necessary for integrating bone and implant material, a time as long as several months is sometimes necessary to achieve fixation (integration) as a complete recovery.

More particularly, Patent Document 1 discloses a laser processing method of providing a surface having undercut and mutual bonding recesses for making "scratch engagement" between implant material and bone easy, so that a time required for integrating the implant material and the bone is shortened with stabilized integration.

Furthermore, Paten Document 2 discloses a laser processing method of cutting dental tissue by applying a laser beam having a wavelength that can be intensively absorbed by hydroxylapatite. Moreover, Patent Document 3 discloses a laser processing method of removing mineralized physiological tissue including dental enamel, dentine, and bone by applying a laser beam having a wavelength that can be intensively absorbed by hydroxylapatite.

Furthermore, Patent Document 4 discloses a laser processing method of removing dental enamel and dentine by using a laser light having a wavelength of 2.0 µm to 3.0 µm. Moreover, Patent Document 5 discloses a laser processing method in which bone material, dental hard material, and arteriosclerotic deposit are peeled off by applying a laser having an emission wavelength of 9.6 µm.

Meanwhile, as a part of researches about implant material that can be easily and strongly integrated with bone, a technology for stabilizing a relative position of the implant material to bone by promoting bone bonding has been being developed. More particularly, a technology for porous biomedical material is expected to achieve preferable cell infiltration characteristic and being more increasingly studied.

The conventional research about the porous biomedical material includes a research about a spongelike structure that cannot retain inherent hardness of ceramics and a research about integration of a porous layer on base material, which leads to complicated fabricating process and variation in quality. The conventional research further includes a research about thermal spraying of apatite particles, which makes it difficult to control size of each hole to be formed, and a research about generation of texture only on the surface of ceramics without examining its internal structure. In addition, in the conventional laser processing methods, while a process for removing implant material or the like is performed, examination about surface modification has not been made at all.

More particularly, Patent Document 6 discloses a technology for setting carbonate apatite to be spongelike porous or spongelike super-porous and then compositing the carbonate apatite to collagen. Moreover, Patent Document 7 discloses a technology for using sponge containing hydroxylapatite and gel-like collagen as bone substitute in plastic surgery.

Furthermore, Patent Document 10 discloses a technology in which dense substrate and porous substrate are formed in separate processes, and then they are dried and sintered while being in contact with each other. Moreover, Patent Document 11 discloses a technology in which apatite particles are mixed dispersed in a glass layer, and after being baking, air holes are exposed by etching. Furthermore, Patent Document 12 discloses a technology for welding hydroxylapatite or tricalcium phosphate on the surface of base material by using plasma arc.

Patent Document 1: Japanese Patent Application Laid-open No. 2002-301091
Patent Document 2: Japanese Patent Application Laid-open No. H4-53550
Patent Document 3: Japanese Patent Application Laid-open No. H4-300535
Patent Document 4: Japanese Patent Application Laid-open No. H2-504478
Patent Document 5: Japanese Patent Application Laid-open No. S62-502170

Patent Document 6: Japanese Patent Application Laid-open No. 2003-169845
Patent Document 7: U.S. Pat. No. 5,071,436 Specification
Patent Document 8: U.S. Pat. No. 5,776,193 Specification
Patent Document 9: U.S. Pat. No. 6,187,047 Specification
Patent Document 10: Japanese Patent Application Laid-open No. S64-37475
Patent Document 11: Japanese Patent Application Laid-open No. H6-7425
Patent Document 12: Japanese Patent Application Laid-open No. S64-52471

DISCLOSURE OF INVENTION

Problem to be Solved by the Invention

However, in the first conventional technology, although the bone growth can be promoted, there is a problem that the bone and the implant material cannot be fixed (integrated) shortly and easily.

Furthermore, in the second conventional technology, because the dental tissue is cut by applying the laser beam having a wavelength that can be intensively absorbed by hydroxylapatite, there is a problem that other materials cannot be cut or integrated shortly and easily.

Moreover, in the third and the fourth conventional technologies, although the mineralized physiological tissue can be cut and removed, there is a problem that these technologies cannot be applied to drilling or integration of a tooth and the implant material.

Furthermore, in the fifth conventional technology, bone and implant material cannot be integrated after a process for removing bone material is performed. Therefore, there is a problem that the bone and the implant material cannot be integrated shortly and easily.

Moreover, in the first conventional technology, a textured portion is provided only on contact surfaces of the implant material and the bone. Therefore, infiltration and penetration of tissue into the inside of the implant material can hardly occur. Thus, there is a problem that the implant material and the bone cannot be integrated shortly and easily.

Furthermore, because the fifth conventional technology is related to the process for removing a hard material and an arteriosclerotic deposit, infiltration and penetration of tissue into the inside of the implant material can hardly occur. Therefore, there is a problem that the implant material and the bone cannot be integrated shortly and easily.

Moreover, in the sixth to the ninth conventional technologies, significance of air bubbles is pointed out as an element of structure of apatite having a preferable cell infiltration characteristic. However, the apatite material is entirely configured to have uniform densities of air bubbles and uniform crystal structures. Therefore, a biological component formed of material having a high density of air bubbles, spongelike material, or porous material may be damaged when being used in an area where strong stress is to be applied. Thus, there is a problem that the biological component can be applied only to areas where relatively weak stress is to be applied. Besides, there is a problem that the process for fabricating the biological component is complicated and thereby quality management is made difficult.

Furthermore, in the tenth to the twelfth conventional technologies, material of a portion to be subjected to surface modification and base material are fabricated in different processes, and a process other than the above fabricating processes is also necessary for integrating the material of the portion to be subjected to the surface modification and the base material. Therefore, the processes become complex. As a result, quality management also becomes complex, resulting in degrading dimensional precision of end products.

The present invention has been made to solve the above problems in the conventional technology and it is an object of the present invention to provide a laser processing apparatus and an osseointegration method that can integrate bone and implant material shortly and easily.

Furthermore, it is an object of the present invention to provide implant material that can be integrated with bone shortly and easily, an implant-material fabrication method, an osseointegration method, and an implant-material fabricating apparatus.

Means for Solving Problem

To solve the above problems and to achieve the object, an osseointegration method according to the present invention is for integrating bone and implant material, including an integrating step of integrating the bone and the implant material by applying a laser beam to a junction of the bone and the implant material.

Effect of the Invention

According to the present invention, a junction of bone and implant material is irradiated with a laser beam so that the bone and the implant material are integrated with each other. Therefore, the bone and the implant material can be integrated shortly and easily.

BRIEF DESCRIPTION OF DRAWINGS

FIG. 2 is a schematic diagram illustrating a processing result when drilling a hole in bone by applying a laser beam.

Figure 1:
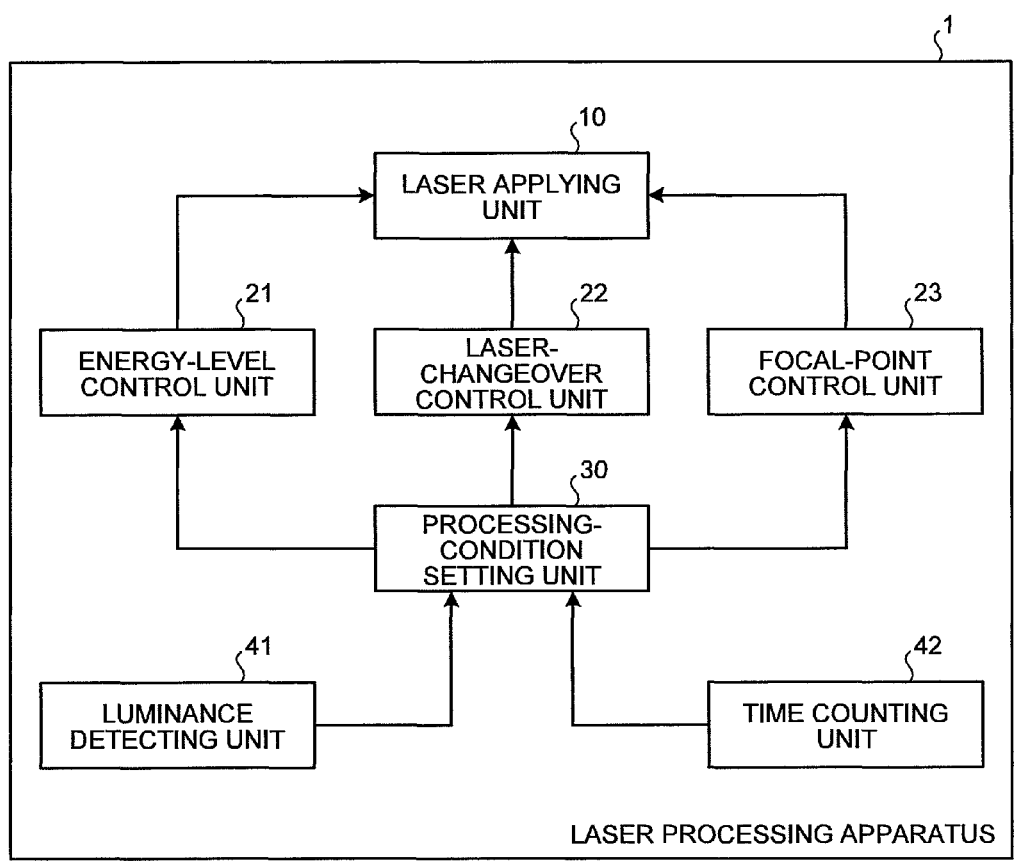
FIG. 1 is a block diagram of a laser processing apparatus according to an embodiment of the present invention.

EXPLANATIONS OF LETTERS OR NUMERALS 1 laser processing apparatus
10 laser applying unit
21 energy-level control unit
22 laser-changeover control unit
23 focal-point control unit
30 processing-condition setting unit
41 luminance detecting unit
42 time counting unit
51 bone
52 implant material
100 foamed layer
101 apatite
150 junction
200 base material

BEST MODE(S) FOR CARRYING OUT THE INVENTION

Exemplary embodiments of a laser processing apparatus, an osseointegration method, implant material, an implant-material fabrication method, and an implant-material fabricating apparatus of the present invention are described in detail below with reference to the accompanying drawings. The present invention is not limited to the following embodiments.

Embodiment 1

FIG. 1 is a block diagram of a laser processing apparatus according to an embodiment of the present invention. The laser processing apparatus 1 includes a laser applying unit 10, an energy-level control unit 21, a laser-changeover control unit 22, a focal-point control unit 23, a processing-condition setting unit 30, a luminance detecting unit 41, and a time counting unit 42.

The energy-level control unit 21, the laser-changeover control unit 22, and the focal-point control unit 23 correspond to a control unit defined in the appended claim, and the luminance detecting unit 41 and the time counting unit 42 correspond to a processing-state detecting unit defined in the appended claim. Further, luminance can be detected through visual examination by a skilled operator depending on the level of skill of the operator. Therefore, an apparatus that does not include the luminance detecting unit 41 is also applicable.

The laser processing apparatus 1 is an apparatus that applies, in an integration process (a bonding process) between implant material (artificial bone or artificial tooth root) and bone, a laser to the implant material and the bone based on predetermined control so that an integrated positional relation of the implant material and the bone is strongly maintained until bone growth is sufficiently promoted and even in the future. Specifically, the laser processing apparatus 1 applies a laser to the implant material and the bone so that the implant material and the bone are drilled and integrated with each other.

The laser applying unit 10 applies a laser to a workpiece such as the implant material and the bone. The laser applying unit 10 is connected to the energy-level control unit 21, the laser-changeover control unit 22, and the focal-point control unit 23, and applies a laser to the implant material and the bone under a predetermined processing condition based on control by the energy-level control unit 21, the laser-changeover control unit 22, and the focal-point control unit 23.

The laser-changeover control unit 22 is configured to change over a type of a laser beam to be applied to a workpiece by the laser applying unit 10, based on an instruction by the processing-condition setting unit 30. The laser-changeover control unit 22 is configured to select one laser beam from among, for example, a $CO_2$ laser, a YAG (Yttrium Aluminum Garnet) laser, a CO laser, a UV (Ultra Violet rays)-YAG laser, a green laser, and an excimer laser, so that the type of a laser beam to be applied to the workpiece by the laser applying unit 10 is changed over.

The focal-point control unit 23 controls a focal point of a laser beam to be applied to the workpiece by the laser applying unit 10, based on an instruction by the processing-condition setting unit 30. The energy-level control unit 21 controls energy level of a laser beam to be applied to the workpiece by the laser applying unit 10, based on an instruction by the processing-condition setting unit 30.

The processing-condition setting unit 30 sends instructions to the energy-level control unit 21, the laser-changeover control unit 22, and the focal-point control unit 23 so that the implant material and the bone are irradiated with a laser under a predetermined processing condition. Specifically, the processing-condition setting unit 30 sends an instruction about the energy level of the laser beam to be applied to the workpiece to the energy-level control unit 21, an instruction about a type of the laser beam to be applied to the workpiece to the laser-changeover control unit 22, and an instruction about the focal point of the laser beam to be applied to the workpiece to the focal-point control unit 23.

The processing-condition setting unit 30 determines a processing condition under which the implant material and the bone are to be irradiated with a laser, based on the luminance of the workpiece received from the luminance detecting unit 41 and a counted time (an elapsed time from a start of laser processing) received from the time counting unit 42. Then, the processing-condition setting unit 30 sends instructions to the energy-level control unit 21, the laser-changeover control unit 22, and the focal-point control unit 23, based on the set processing condition.

The luminance detecting unit 41 detects, as a processing state of the workpiece, the luminance of the workpiece (the luminance of a portion of the workpiece to be irradiated with a laser beam), and then sends the luminance to the processing-condition setting unit 30. The time counting unit 42 counts, as a processing state of the workpiece, an elapsed time from a start of laser processing, an elapsed time from a start of drilling of the implant material, an elapsed time from a start of drilling of the bone, or an elapsed time from a start of irradiation of a junction (an integrated portion between the bone and the implant) with a laser beam for integrating the implant material and the bone, and then sends the elapsed time being counted to the processing-condition setting unit 30.

As for the implant material, metal such as titanium or stainless, plastic such as resin, bioactive ceramics such as apatite ceramics, or bioinert ceramics such as alumina ceramics is used. Materials other than the above can also be used as the implant material.

A laser processing process performed by the laser processing apparatus 1 is described in detail below. The laser applying unit 10 of the laser processing apparatus 1 employs, as a laser beam, energy density of $10^3$ W/cm$^2$ or higher at a focused point with a diameter of 0.3 mm or smaller, which is high energy density. Accordingly, an area to be processed with a laser beam can be narrowed (be confined to a limited area), and thereby, a drilling process or a melt process on the workpiece can be performed in a short time. The laser processing apparatus 1 can control a time for melting the workpiece (melt time) and an area of the workpiece to be melted, because of selection (setting) of the processing condition (output condition of a laser beam) by the processing-condition setting unit 30. Further, the laser processing apparatus 1 can perform the drilling process or the melt process on a wide varieties of workpiece such as metal, plastic, and ceramics, because of selection of the processing condition by the processing-condition setting unit 30.

Next, as an example of the detailed laser processing process performed by the laser processing apparatus 1, a drilling process on the workpiece is described below. FIG. 2 is a schematic diagram illustrating a processing result when drilling a hole in bone by applying a laser beam. Here, a top surface of bone obtained when the bone has a thickness of 10 mm and is irradiated with a $CO_2$ laser (output of the laser beam is 500 W) is illustrated. In FIG. 2, outline images of holes (results with increased hole diameters) when drilling the holes in the bone while setting a beam-ON time (irradiation ON) of the applied laser beam to 0.5 second and 1.0 second are illustrated with respect to each focal point Z.

The focal point Z of zero indicates a case when the focal point is on the surface of the bone. The focal point Z of 5 indicates a case when the focal point is on a plane shifted upward by 5 mm from the surface of the bone. The focal point Z of 10 indicates a case when the focal point is on a plane shifted upward by 10 mm from the surface of the bone.

As shown in FIG. 2, as the amount of shift of the focal point increases, a beam spot size of the laser beam on the surface of the bone increases while its energy density decreases. Thus, when processing with an upward focal point, a larger hole diameter and a shallower hole depth than those obtained through processing with a less upward focal point are obtained. In other words, with the upward focal point, as the beam spot size increases, the hole diameter increases while the hole depth decreases.

When treating bone by using the laser processing apparatus 1, a medical treatment time can be effectively shortened and negative effects on normal cells can be effectively suppressed by suppressing thermal effects of an area to be processed by laser processing.

In this example, processing (control) is performed so that the hole diameters are in a range from about 0.4 mm to 1.5 mm under all processing conditions (the focal point of 0 mm to 10 mm and the beam-ON time (a laser irradiation time) of 0.5 second and 1.0 second), whereby thermal effects generated around holes can be limited within a limited area in a range from about 0.1 mm to 0.3 mm.

When it is necessary to increase the hole diameter than the hole diameter obtained at the focal point of 10 mm shown in FIG. 2, the focal point should preferably be set on a plane upper than that of the focal point of 10 mm. Furthermore, when it is necessary to decrease the hole diameter than the hole diameter obtained with the beam-ON time of 0.5 second shown in FIG. 2, the beam-ON time should preferably be set shorter than 0.5 second.

In the drilling process using a laser beam, because energy of the laser beam is used up and decayed due to processing while the processing continues inwardly from the surface of a workpiece, the hole diameter is reduced inwardly. Even when the drilling process is performed by using a YAG laser with a wavelength of 1.06 μm that is one-tenth of the wavelength of the $CO_2$ laser, the drilling process can be performed with less thermal effects, similar to the case of the $CO_2$ laser.

Further, in the drilling process, when a UV-YAG laser, an excimer laser, each having a wavelength within the ultraviolet range, or a green laser having a wavelength within the visible light range is used, bond cleavage occurs because of electron excitation due to an ultraviolet light or a visible light, which leads to photochemical processing (ablation processing). Therefore, thermal effects on bone and implant material can be more suppressed than those suppressed when a $CO_2$ laser or a YAG laser, each being an infrared laser, is used.

Furthermore, when drilling a hole in bone or implant material by using a UV-YAG laser, an excimer laser, or a green laser, a tinier hole can be processed than that processed by using a $CO_2$ laser or a YAG laser, each being an infrared laser. Thus, regardless of the type of a laser to be used (a $CO_2$ laser or a YAG laser, each being an infrared laser, and a UV-YAG laser, an excimer laser, or a green laser, each being an ultraviolet laser), it is possible to perform the drilling process on bone and implant material with less thermal effects.

Any laser beams such as a $CO_2$ laser, a YAG laser, an excimer laser, and a UV-YAG laser can be preferably used for the drilling process. On the contrary, a laser beam having an infrared wavelength, such as a $CO_2$ laser and a YAG laser, can be preferably used for an integration process.

When performing the drilling process and the integration process sequentially on a workpiece by the laser processing apparatus 1, both processing can be performed by using a laser. Alternatively, it is possible to perform a process for drilling a hole by cutting in advance to suppress thermal effects caused by drilling, and then apply a laser beam for integration through the hole.

Figure 3:
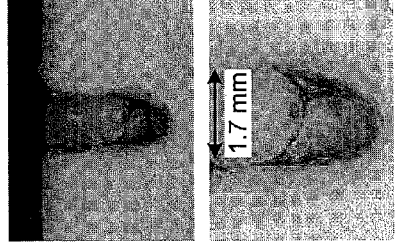
FIG. 3 is a schematic diagram illustrating a processing result when melting implant material by applying a laser beam.

Next, the integration process on implant material performed by using a laser beam emitted by the laser processing apparatus 1 is described below. FIG. 3 is a schematic diagram illustrating a processing result when melting implant material by applying a laser beam. Here, examples of a top surface and a cross section of implant material made of apatite that is one of ceramics (examples of a melted state of apatite observed under various thermal cycles) are illustrated.

In images (top surface) shown in FIG. 3, holes are shown in the center areas while blackened areas around the holes indicate melted areas. The center areas irradiated with a laser beam become hot, so that the workpiece is melted and then vaporized in short bursts, whereby the holes are formed. On the other hand, the areas around the holes are not vaporized during thermal cycles, that is, the areas are melted and then coagulated. Thus, in a process for melting the implant material (apatite), a melted area can be expanded by changing emission condition of a laser beam.

In this example, the states of the melted areas in the following conditions are illustrated. That is, a YAG laser of a wavelength of 1.06 μm is used, output of an irradiating laser beam is set to 250 W, the focal point Z of 5 mm is set unchanged, and the beam-ON time is changed to 0.5 second, 9.0 seconds, and 12.0 seconds. Here, main component of the apatite is calcium phosphate and frit is composed of cordierite.

When the laser irradiation time is increased, a melted area of a portion irradiated with a laser beam is extended from 1.7 mm to 2.3 mm. While it is not shown in the drawing, the melted area can be extended also by changing the focal point. Further, a melted depth can be extended by changing a laser output.

Generally, when ceramics is melted by heating a limited area, crack often occurs due to expansion and contraction of a workpiece. Therefore, the entire workpiece is heated to be melted and integrated in a furnace. However, in surgical operation or the like, such a processing method can hardly be employed because it is spatially difficult and it causes negative effects on a living body. The laser processing performed by the laser processing apparatus 1 (the laser applying unit 10) according to the embodiment enables melting of ceramics in a narrow space, without causing negative effects on a living body, and without causing crack, even in surgical operation. In other words, due to heating by a laser beam emitted by the laser processing apparatus 1 (the laser applying unit 10), processing can be completed such that an area of a workpiece to be heated is limited within a range that prevents crack spatially and temporally, based on an instruction about the processing condition from the processing-condition setting unit 30 (based on control by the energy-level control unit 21, the laser-changeover control unit 22, and the focal-point control unit 23), which is effective as a surgical operation method.

Furthermore, because the melted area is more extended as the laser irradiation time is set longer, the laser irradiation time is changed depending on strength of integration. In other words, the processing-condition setting unit 30 sets a longer laser irradiation time when integration with increased strength is required, and sets a shorter laser irradiation time when integration with decreased strength is required. The processing-condition setting unit 30 can set the laser irradiation time based on an instruction from a user (an instruction from an input unit), or can set the laser irradiation time based on luminance detected by the luminance detecting unit 41.

Moreover, the laser processing apparatus 1 can extend the melted area by adjusting a focal point or selecting a focusing optical component. Therefore, the processing-condition setting unit 30 selects a focal point corresponding to a melted area as a processing condition, and instructs the processing condition to the focal-point control unit 23. Furthermore, the laser processing apparatus 1 can be configured so that a focusing optical component can be selected for each laser processing depending on a melted area. For example, the laser processing apparatus 1 can be configured such that a focusing optical component is automatically changed based on an instruction from the processing-condition setting unit 30. It is also possible for a user of the laser processing apparatus 1 to manually change a focusing optical component in advance.

The processing-condition setting unit 30 also sets a processing condition such that drilling can be performed at energy level at which a workpiece does not cause harmful side effects, and then sends the processing condition to the energy-level control unit 21.

The integration process (integration between two different material) performed on a workpiece by the laser processing apparatus 1 is described below. An integration process in which a laser is applied to a junction of bone and implant material is described below.

Figure 4:
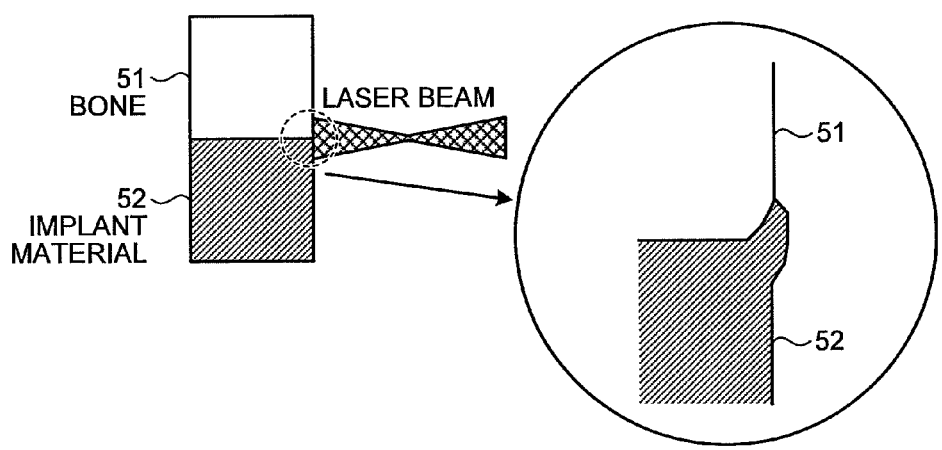
FIG. 4 is a schematic diagram for explaining an integration process when a laser beam is applied to a junction of bone and implant material.

FIG. 4 is a schematic diagram for explaining an integration process when a laser beam is applied to a junction of bone and implant material. More particularly, the integration process is performed on a workpiece by using a bone 51 made of beef bone having a thickness of 3 mm and an implant material 52 made of ceramics containing calcium phosphate as main component. Furthermore, the integration process is performed on a workpiece such that a $CO_2$ laser having a wavelength of 10.6 µm is used as a laser beam and the processing condition is set such that a laser output is 250 W, a laser irradiation time is 0.5 second, and a focal point is shifted upward by 3 mm.

When the laser processing apparatus 1 applies a laser beam to a workpiece such that a junction of the bone 51 and the implant material 52 is irradiated with the laser beam, a hole is drilled in the bone 51 instantly, and the implant material 52 is melted. When the laser processing apparatus 1 continues laser irradiation, the melted material of the implant material 52 is filled in a hole of the bone 51. Thereafter, the melted implant material 52 is coagulated, whereby integration between the bone 51 and the implant material 52 is completed. Thus, the laser processing apparatus 1 utilizes a difference in boiling points of the bone 51 and the implant material 52. In other words, because a boiling point of the bone 51 is lower than that of the implant material 52, a hole is drilled in the bone 51 while the implant material 52 is just melted and a hole is not drilled in the implant material 52 due to laser irradiation by the laser processing apparatus 1. Then, the implant material 52 having a high boiling point flows into the hole of the bone 51 having a low boiling point, whereby the bone 51 and the implant material 52 are integrated.

When the workpiece is integrated by setting such that the junction of the bone 51 and the implant material 52 is to be irradiated with a laser beam, the luminance detecting unit 41 of the laser processing apparatus 1 detects luminance of the area to be irradiated with the laser beam (the junction of the bone 51 and the implant material 52). The luminance detected by the luminance detecting unit 41 is sent to the processing-condition setting unit 30.

The processing-condition setting unit 30 selects (sets) a laser beam, energy level, and a focal point corresponding to the area to be irradiated with the laser beam based on the luminance detected by the luminance detecting unit 41. At this state, the processing-condition setting unit 30 can select a laser beam, energy level, and a focal point by using previously-set processing conditions (e.g., a type of the implant material 52, strength of the bone 51, a processing area on the workpiece, or desired strength of integration).

The processing-condition setting unit 30 instructs laser irradiation on the workpiece for a predetermined time based on the laser irradiation time counted by the time counting unit 42 and the luminance detected by the luminance detecting unit 41. As a result, the integration between the bone 51 and the implant material 52 is completed.

In this manner, because a laser beam is used for integrating the bone 51 and the implant material 52, a preferable (strong) junction can be instantly obtained. Besides, the processing-condition setting unit 30 sets the processing condition based on luminance detected by the luminance detecting unit 41 and a time counted by the time counting unit 42, and then laser irradiation is performed. Therefore, laser irradiation suitable for a workpiece can be performed. As a result, integration can be performed in a manner suitable for each workpiece (the junction of the bone 51 and the implant material 52).

Furthermore, when the workpiece is integrated by using the laser processing apparatus 1, a preferable junction can be obtained regardless of thicknesses of the bone 51 and the implant material 52. Therefore, the integration process using a laser beam can be used for various biological regions.

While it is described that the implant material 52 is made of calcium phosphate, ceramics other than calcium phosphate can be used. Besides, even when the laser processing apparatus 1 employs a YAG laser as a laser beam, because a YAG laser enables fiber transmission, it can be more easily applied to medical operations than a $CO_2$ laser. Further, when a laser beam is applied to a junction of bone and implant material, and even if the laser processing apparatus 1 employs a YAG laser as a laser beam, a preferable junction can be obtained similar to the case using a $CO_2$ laser.

Next, an integration process in which a laser beam is applied to a contact surface between the bone 51 and the implant material 52 in a direction substantially normal to the contact surface (laser irradiation on a joint) is described below. Here, an example for integrating the bone 51 and the implant material 52 by applying a laser to a top surface of a workpiece (from the side of the bone 51) in which the implant material 52 is arranged on a bottom portion and the bone 51 is arranged on a top portion is firstly described. Then, an example for integrating the bone 51 and the implant material 52 by applying a laser to a top surface of a workpiece (from the side of the implant material 52) in which the bone 51 is arranged on a bottom portion and the implant material 52 is arranged on a top portion will be described later.

Figure 5:
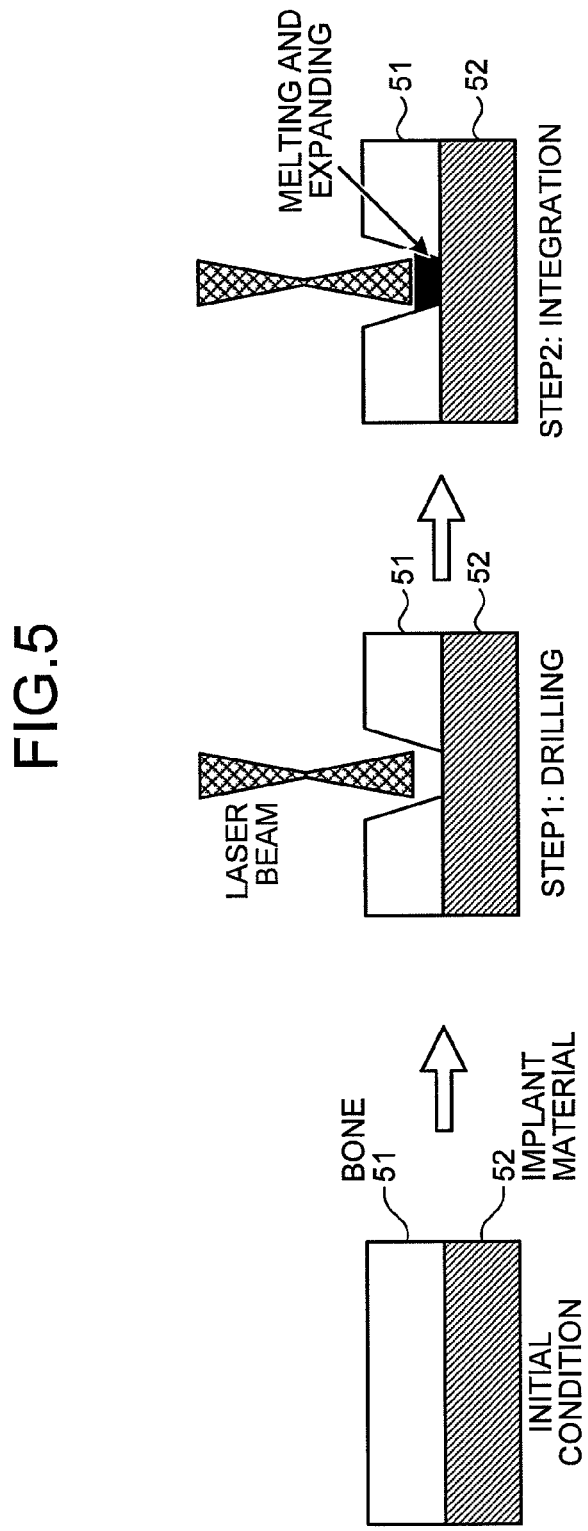
FIG. 5 is a schematic diagram for explaining an integration process when a laser beam is applied to a top surface of a workpiece in which implant material is arranged on a bottom portion and bone is arranged on a top portion.

FIG. 5 is a schematic diagram for explaining an integration process when a laser beam is applied to a top surface of a workpiece in which the implant material is arranged on a bottom portion and the bone is arranged on a top portion. The integration process is performed on a workpiece by using the bone 51 made of beef bone having a thickness of 3.0 mm and the implant material 52 made of ceramics containing calcium phosphate as main component.

The bone 51 and the implant material 52 are brought into close contact with each other in advance. The laser processing apparatus 1 drills, as the first step, a hole in the bone 51 by applying a laser beam to the bone 51 (the state shown in the middle in FIG. 5). Then, as the second step, the laser processing apparatus 1 integrates the bone 51 and the implant material 52 by applying a laser beam to the implant material 52 through a hole (a drilled portion) of the bone 51 (the state shown on the right side in FIG. 5).

The processing-condition setting unit 30 of the laser processing apparatus 1 sets a processing condition for the workpiece based on luminance detected by the luminance detecting unit 41, a time counted by the time counting unit 42, and a previously-set processing condition. The processing-condition setting unit 30 can set a processing condition for the workpiece based on a close contact state between the bone 51 and the implant material 52 or requested strength (strength required for integration between the bone 51 and the implant material 52 (after processing)). The laser processing apparatus 1 performs, as the first step for drilling a hole in the bone 51, laser processing on the bone 51 under a processing condition set such that a laser output is 400 W, a focal point is shifted upward by 30 mm, and an irradiation time is 0.2 second.

When drilling of a hole in the bone 51 is completed by the laser processing apparatus 1, luminance detected by the luminance detecting unit 41 changes. Accordingly, the laser processing apparatus 1 performs, as the second step for integrating the bone 51 and the implant material 52 by applying a laser beam to the hole of the bone 51 (the surface of the implant material 52), laser processing under a processing condition set such that a laser output is 500 W, a focal point is shifted upward by 30 mm, and an irradiation time is 1.0 second.

The laser processing apparatus 1 can change the processing condition used at the second step based on a time counted by the time counting unit 42. In other words, the processing-condition setting unit 30 can be configured to calculate a time for completing the drilling of a hole in the bone 51 in advance based on the previously-set thickness of the bone 51, the previously-set type of the implant material 52, or the processing condition set at the first step, and change over a processing condition used at the second step based on the calculated time.

When the bone 51 (beef bone) is observed after being subjected to the laser processing process at the first step by the laser processing apparatus 1, there is a hole in a tapered manner in which a hole diameter on the surface to which a laser beam is applied (a top surface of a cylinder) is 2.6 mm and a hole diameter on the side opposite to the surface to which the laser beam is applied (bottom surface of the cylinder) is 1.0 mm.

Further, when the workpiece (processed material) is observed after being subjected to the laser processing process at the second step by the laser processing apparatus 1, it is found that the bone 51 and the implant material 52 are strongly integrated in preferable condition. This is because, when a laser beam is applied to a top surface of the bone 51, bone component is mixed to a melted area of the implant material 52 and a mixed area is expanded to fill the hole of the bone. In other words, the laser processing apparatus 1 applies a laser beam to a workpiece so that the expanded implant material 52 is filled in the hole drilled in the bone 51. Thus, melted material of the implant material 52 is expanded to be integrated with the hole of the bone 51 that has been processed so that the hole has a tapered shape through the laser processing by the laser processing apparatus 1. As a result, a junction can have high integration strength with regard to tension strength and peel strength.

When a laser beam is applied to a top surface of a workpiece in which implant material is arranged on a bottom portion and bone is arranged on a top portion, and even if the laser processing apparatus 1 employs a YAG laser as a laser beam, a preferable junction can be obtained similar to the case using a $CO_2$ laser.

Figure 6:
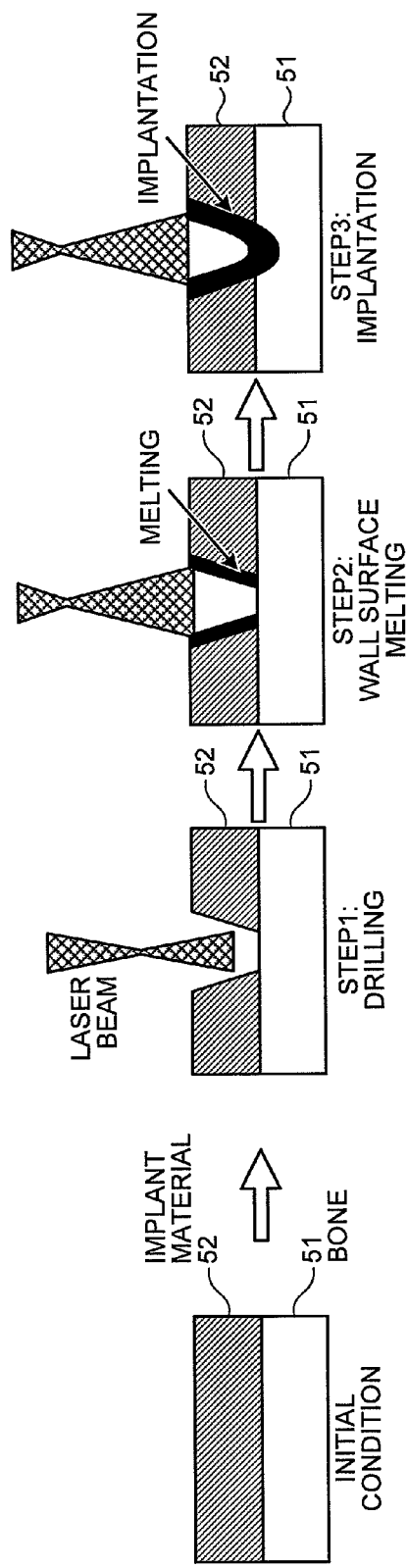
FIG. 6 is a schematic diagram for explaining an integration process when a laser beam is applied to a top surface of a workpiece in which bone is arranged on a bottom portion and implant material is arranged on a top portion.

FIG. 6 is a schematic diagram for explaining an integration process when a laser beam is applied to a top surface of a workpiece in which the bone is arranged on a bottom portion and the implant material is arranged on a top portion. Here, the integration process is performed on a workpiece by using the bone 51 made of beef bone having a thickness of 3.0 mm and the implant material 52 made of ceramics containing calcium phosphate as main component. The laser processing apparatus 1 performs a laser processing by using a $CO_2$ laser having a wavelength of 10.6 μm or the like.

When the implant material 52 is on the side to be irradiated with a laser beam, the bone 51 and the implant material 52 are integrated through an integration process with phenomenon different from that described with reference to FIG. 5. Specifically, when the implant material 52 is on the side to be irradiated with a laser beam, a hole is drilled in the implant material 52 due to a laser beam (the first step). Then, wall surface of the hole of the implant material 52 is melted due to the laser beam (the second step). By continuing laser irradiation, a hole is drilled in the bone 51 due to the laser beam while melted material of the implant material 52 is filled in the hole of the bone 51 (the third step).

More particularly, when drilling of a hole in the implant material 52 is completed by the laser processing apparatus 1, luminance detected by the luminance detecting unit 41 changes. Accordingly, the laser processing apparatus 1 performs, as the second step for melting the wall surface of the hole of the implant material 52 by applying a laser beam to the hole of the implant material 52 (the surface of the bone 51), laser processing under a predetermined processing condition. Further, when the wall surface of the hole of the implant material 52 is melted by the laser processing apparatus 1, luminance detected by the luminance detecting unit 41 changes. Accordingly, the laser processing apparatus 1 performs, as the third step for drilling a hole in the bone 51 and filling the implant material 52 in the hole of the bone 51, laser processing under a predetermined processing condition.

Similar to the integration process described with reference to FIG. 5, the laser processing apparatus 1 can change the processing condition used at the second and the third steps based on a time counted by the time counting unit 42. In other words, the processing-condition setting unit 30 can be configured to calculate a time for completing the drilling of a hole in the bone 51 in advance based on the previously-set thickness of the bone 51, the previously-set type of the implant material 52, or the processing condition set at the first step, and change over processing conditions used at the second and the third steps based on the calculated time.

When a laser beam is applied to a top surface of a workpiece in which bone is arranged on a bottom portion and implant material is arranged on a top portion, and even if the laser processing apparatus 1 employs a YAG laser as a laser beam, a preferable junction can be obtained similar to the case using a $CO_2$ laser.

Next, an integration process for applying a laser to the bone 51, where the implant material 52 and a thick plate of the bone 51 (a plate having a thick thickness) are used, is described below. Specifically, an example for integrating a beef bone block (the bone 51) having a thickness of 10 mm and the implant material 52 is described below.

Figure 7:
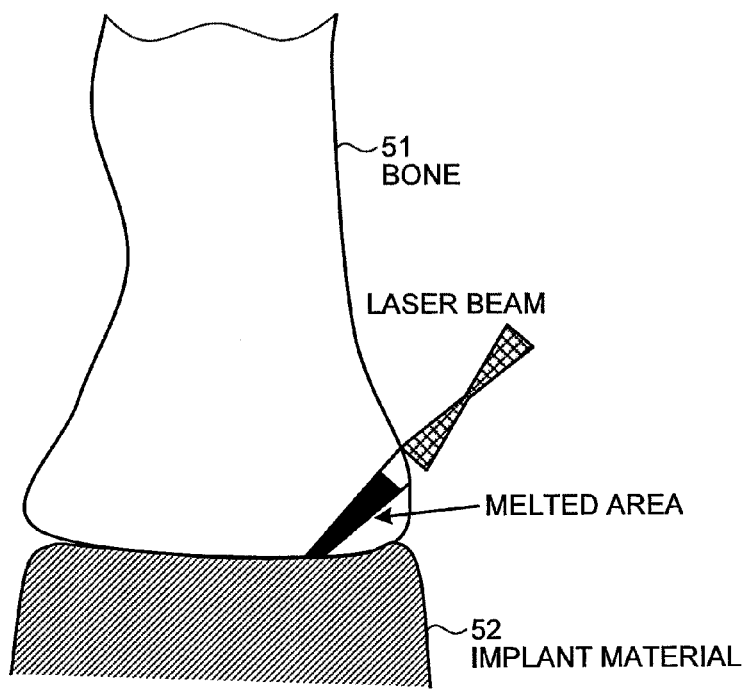
FIG. 7 is a schematic diagram for explaining an integration process between thick bone and implant material.

FIG. 7 is a schematic diagram for explaining an integration process between a thick bone and the implant material. Here, the integration process is performed on a workpiece by using the implant material 52 made of ceramics containing calcium phosphate as main component.

When integrating the bone 51 and the implant material 52 by applying a laser to a top surface of a workpiece (from the side of the bone 51) in which the implant material 52 is arranged on a bottom portion and a thick plate of the bone 51 is arranged on a top portion, the laser processing apparatus 1 performs a laser processing by using a $CO_2$ laser having a wavelength of 10.6 μm or the like. Here, to reduce a time for integration and a time for drilling a hole in the bone 51, a process for drilling a hole in the bone 51 and an integration process (a process for integrating the bone 51 and the implant material 52) are performed under the same processing condition.

The laser processing apparatus 1 performs a laser processing under a processing condition set such that a laser output is 500 W, a focal point is shifted upward by 20 mm, an irradiation angle (an irradiation angle to the top surface of the implant material 52) is 45 degrees, and a laser irradiation time is 1.0 second. In this example, the laser processing apparatus 1 is caused to apply a laser beam to a processing point shifted by 0.3 mm towards the side of the bone 51 from a junction of the bone 51 and the implant material 52.

A process for integrating the bone 51 and the implant material 52 is the same as the process described with reference to FIG. 4. That is, a hole is drilled in the bone 51 by applying a laser beam (the first step), and the implant material 52 melted due to the laser beam is expanded towards the hole of the bone and then integrated (the second step). Thus, in the integration process shown in FIG. 7, the laser processing apparatus 1 uses a laser beam to integrate the bone 51 and the implant material 52. Therefore, a preferable junction can be obtained instantly.

Figure 8:
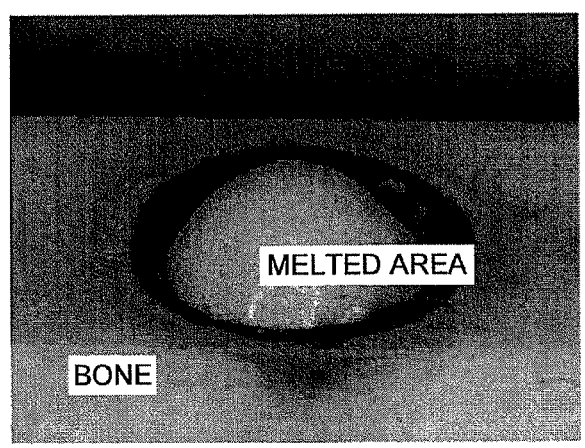
FIG. 8 is an image of a thin plate of bone integrated with implant material.

Next, an integration process for applying a laser to the bone 51, where the implant material 52 and a thin plate of the bone 51 (a plate having a thin thickness) are used, is described below. FIG. 8 is an image of a thin plate of bone integrated with implant material. As shown in FIG. 8, when a thin plate of the bone 51 is used, similar to when the thick plate of the bone 51 is used, the laser processing apparatus 1 uses a laser beam to integrate the bone 51 and the implant material 52, whereby a preferable junction can be obtained instantly. In other words, the laser processing apparatus 1 can integrate the bone 51 and the implant material 52 by using a laser beam regardless of the thickness of the bone 51.

When the thick plate of the bone 51 or the thin plate of the bone 51 and the implant material 52 are integrated, and even if the laser processing apparatus 1 employs a YAG laser as a laser beam, a preferable junction can be obtained similar to the case using a $CO_2$ laser.

The laser processing apparatus 1 can employ arbitrary laser oscillators and focusing optical components. The laser processing apparatus 1 can form a tiny hole, through a drilling process, by using a laser oscillator or a focusing optical component that can achieve high energy density.

Furthermore, the laser processing apparatus 1 can reduce thermal effects on the bone 51 or the implant material 52 by using a laser oscillator or a focusing optical component that can achieve high energy density.

Meanwhile, luminance around a junction is different in a case where a preferable junction is obtained and in a case where a less preferable junction is obtained. Therefore, if laser processing is performed without monitoring luminance, laser energy larger than the amount of heat necessary to be conducted for a drilling process or an integration process is applied to the bone 51 or the implant material 52. As a result, an area to be subjected to thermal effects increases in a workpiece, and melted material cannot be coagulated while being dispersed, leading to worse integration. On the other hand, in the laser processing apparatus 1 according to the embodiment, the luminance detecting unit 41 detects (monitors) luminance, and a processing condition is set based on the detected luminance. Therefore, a preferable junction can be obtained.

Further, when the implant material 52 is made of apatite, the implant material 52 has relatively weak resistant to thermal shock. Therefore, as the amount of heat to be conducted increases, crack is more likely to occur on the implant material 52. In the laser processing apparatus 1 according to the embodiment, because a processing condition is set based on luminance detected by the luminance detecting unit 41, a stable and a preferable junction can be obtained even when the implant material 52 is made of apatite.

While the laser processing apparatus 1 according to the embodiment is configured to include the luminance detecting unit 41 and the time counting unit 42 in the embodiment, the configuration without the luminance detecting unit 41 and the time counting unit 42 can be applied. In this case, a user of the laser processing apparatus 1 detects a processing state of a workpiece by visual contact, and the processing-condition setting unit 30 sets a processing condition based on input of instruction information from the user. In other words, the laser processing apparatus 1 sets the processing condition for the workpiece without detection of the processing state by the luminance detecting unit 41 and the time counting unit 42.

Regarding a workpiece to be processed by the laser processing apparatus 1, the bone 51 and the implant material 52 can be arranged such that either one is arranged on a top portion or a bottom portion while the other one is arranged on the remaining portion. Furthermore, the bone 51 and the implant material 52 can be joined by lap joint or butt joint. Moreover, while beef bone is used as the bone in the embodiment, the laser processing apparatus 1 can perform laser processing on bone of any animals and humans. Furthermore, part or all of the processes performed by the laser processing apparatus 1 described such that they are performed automatically in the embodiment can be performed manually.

Moreover, the laser processing apparatus 1 can integrate the bone 51 and the implant material 52 within a body of an animal, or outside of the body of the animal or human by taking out the bone 51 from the body of the animal or human. When the bone 51 and the implant material 52 are integrated after the bone 51 is taken out of the body of the animal or human, the integrated bone 51 and the implant material 52 is returned to the inside of the body of the animal or human as appropriate.

In this manner, according to the first embodiment, a laser beam such as a $CO_2$ laser or a YAG laser is applied for integrating bone and implant material. Therefore, the bone and the implant material can be integrated shortly and easily.

Furthermore, the processing-condition setting unit 30 sets a processing condition based on luminance detected by the luminance detecting unit 41 and a time counted by the time counting unit 42, and then a laser beam is applied to a workpiece. Therefore, laser irradiation and an integration process can be performed appropriately depending on a workpiece.

Moreover, the processing-condition setting unit 30 sets, as a processing condition, energy level of a laser beam, a type of a laser beam, a focal point, and an irradiation time of a laser beam, and then a laser beam is applied to a workpiece based on the set processing condition. Therefore, a drilling process and an integration process can be performed stably and appropriately for each drilling process and integration process on a workpiece.

Furthermore, because the laser processing apparatus 1 can integrate bone and implant material shortly and easily, it is possible to prevent change in relative positions of the implant material and the bone being integrated with each other while medical treatment for integrating the bone and the implant material is performed. Therefore, the medical treatment can be performed shortly and easily. Moreover, a large-scale fixture that has been necessary in conventional medical treatment for integration is not necessary. As a result, it is possible to provide comfortable life while medical treatment is being performed.

Embodiment 2

Next, a second embodiment of the present invention is described below with reference to FIGS. 9 to 14. In the second embodiment, a laser beam is applied to the implant material 52 in which a non-foamed layer is used as base material, and a foamed layer (a processed layer modified from the non-foamed layer) is made on a surface layer of the non-foamed layer. By forming the foamed layer, implant material having a two-layer structure containing the foamed layer and the non-foamed layer is generated.

Conventionally, when fabricating foamed ceramics, it is necessary to add, during a process for melting ceramics made of expandable material, component that causes the ceramics to produce gas (gas producing component). Examples of the gas producing component include silicon carbide and silicon nitride. As for silicon carbide, fine particles having particle sizes of 10 µm or smaller are used.

In a process for fabricating such foamed ceramics, components of expandable material and non-expandable material are mixed and adjusted in a predetermined ratio. Then, each of the obtained expandable material and the obtained non-expandable material is granulated into particles through a spray drier or the like. The granulated particles of both materials are mixed, and mixture as molding material is molded and baked. The baking temperature at this time is set to a temperature at which the gas producing component is decomposed to produce gas and in a temperature range in which preferable air bubbles (wall bubbles) are generated. More particularly, when silicon carbide is used as the gas producing component, the silicon carbide is decomposed to produce a gas (carbon monoxide) due to the baking, and air bubbles are generated in a sintered layer due to the gas.

In the embodiment, the bone is burned by an application of a laser beam or the like, and the implant material is sintered in a gas atmosphere produced by burning the bone. As a result, a foamed layer is made through confinement and coagulation of air bubbles in the implant material.

If the baking temperature of the mixture (the particles of the expandable material and the non-expandable material) is set lower than 1000° C., air bubbles cannot be generated because sufficient viscosity cannot be obtained on base material. On the other hand, if the baking temperature of the mixture is set higher than 1300° C., low viscosity is obtained on base material, so that generated air bubbles are associated with one another, resulting in coarse bubbles. As a result, strength of sintered material decreases.

Next, as an example of the implant material according to the second embodiment, apatite that has the same characteristics (function) of that of the foamed ceramics is described below. Particularly, the structure of the apatite according to the second embodiment is firstly described, and an apparatus and a method of fabricating the apatite will be described later.

Figures 9, 10:
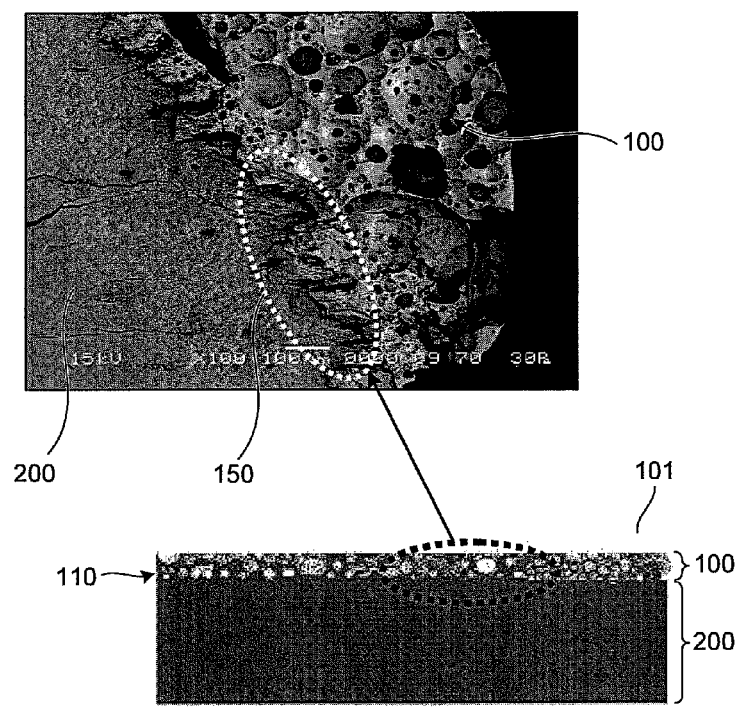
FIG. 9 is a schematic diagram of a structure of apatite according to a second embodiment of the present invention.
FIG. 10 is a schematic diagram illustrating an example of a result of an analysis of components.

FIG. 9 is a schematic diagram of a structure of an apatite according to the second embodiment. The apatite 101 shown in FIG. 9 has a two-layer structure in which a foamed layer is made through surface treatment on a portion (a junction to be integrated with bone) of a surface layer of a non-foamed layer (a base layer).

A foamed layer 100 containing air bubbles that are generated because of surface treatment by application of high energy to a limited area is made on the surface layer of a base material 200 (apatite base material that is a non-foamed layer). The air bubbles in the foamed layer 100 have diameters of, for example, from 10 µm to 500 µm, by which bone cell proliferation to the foamed layer 100 can be promoted when the foamed layer 100 is integrated with bone.

A junction 150 between the foamed layer 100 and the base material 200 that is a non-foamed layer (e.g., the implant material 52) is structured such that each contact surface is textured to be engaged with each other so that strong integration is obtained. The base material 200 has a dense structure with sufficient resistant to stress.

When making the apatite 101, bone (e.g., the bone 51) as the gas producing component is arranged on a surface layer area of the base material 200 (around a processing area of the base material 200, such as a top surface area or a side surface area). Then, the bone is burned by applying a laser beam, and the base material 200 (the molded dense substrate) is melted in an atmosphere containing the combustion gas component. As a result, the component of the bone is mixed in the foamed layer 100.

FIG. 10 is a schematic diagram illustrating an example of a result of an analysis of components of the foamed layer. Specifically, in FIG. 10, an example of a result obtained by analyzing components (Vol %) of the foamed layer 100 is illustrated. The foamed layer 100 contains, as components, Ca (calcium), C (carbon), O (oxygen), P (phosphorous), Mg (magnesium), Al (aluminum), and Si (silicon). The concentrations of Ca, C, and O approximately correspond to the concentrations in bone, respectively, and the concentration of P is slightly reduced from its concentration in bone. The reduction of P is caused by sublimation of P due to high energy generated when the base material 200 is melted.

After the bone is burned and the base material 200 is melted, the surface of the foamed layer 100 (a contact surface with respect to the bone) is lapped or ground. Therefore, confined air bubbles on the surface of the foamed layer 100 are grinded. Accordingly, surfaces of the confined air bubbles are exposed. As a result, the apatite (the foamed apatite)

according to the second embodiment that has a surface modified layer to be a contact surface to the bone is obtained.

In the embodiment, because the apatite contains components substantially similar to those of bone, cell infiltration characteristic acts on the apatite when the bone and the apatite are integrated. As a result, the bone and the apatite 101 can be integrated in a short time. Furthermore, because the surfaces of the confined air bubbles are exposed on the surface of the foamed layer 100, the bone and the apatite 101 can be integrated in a short time compared to when the surfaces of the confined air bubbles are not exposed.

When burning the bone and melting the base material 200, if an electron beam or a plasma arc is used as a heat source, the same effects as that when burning the bone and melting the base material 200 by using a laser beam can be obtained. In this case, the laser applying unit (heat-source applying unit) 10 emits a heat source such as an electron beam or a plasma arc. If a plurality of heat sources is available, the laser-changeover control unit (heat-source changeover control unit) 22 changes a type of the heat source. By adjusting a processing condition (thermal energy of the heat source to be applied to the bone and the base material 200) as appropriate, the number and sizes of air bubbles in the foamed layer 100 can be adjusted. Thus, by adjusting the processing condition depending on a use purpose of the apatite 101, the apatite 101 having a desired property can be obtained. More particularly, by adjusting thermal energy (the processing condition) of the heat source, such as a laser beam, an electron beam, or a plasma arc, as appropriate, the apatite 101 having a desired quality can be obtained. In the following description, a process for fabricating the apatite 101 is explained, in which a laser processing apparatus is used as an example of an apparatus for fabricating the apatite 101. A configuration of the laser processing apparatus is firstly explained and a process for fabricating the apatite 101 will be explained later.

The laser processing apparatus according to the second embodiment of the present invention is configured to be the same apparatus as the laser processing apparatus 1 shown in FIG. 1 in the first embodiment. Explanation about the constituent elements that perform the same functions as the laser processing apparatus 1 is omitted, and functions different from those of the laser processing apparatus 1 according to the first embodiment are described below. Here, luminance can be detected through visual examination by a skilled operator depending on the level of skill of the operator. Therefore, an apparatus that does not include the luminance detecting unit 41 is also applicable.

The luminance detecting unit 41 according to the embodiment detects, as a processing state of a workpiece, luminance of the workpiece, and sends the detected luminance to the processing-condition setting unit 30. The time counting unit 42 counts, as a processing state of a workpiece, an elapsed time from a start of laser processing (an elapsed time from a start of laser irradiation to the implant material 52), and sends the elapsed time being counted to the processing-condition setting unit 30.

A laser processing process performed by the laser processing apparatus 1 is described below. The laser applying unit 10 of the laser processing apparatus 1 employs, as a laser beam, energy density of $10^3$ W/cm$^2$ or higher at a focused point with a diameter of 0.3 mm or smaller, which is high energy density. Accordingly, an area to be processed with a laser beam can be narrowed (be confined to a limited area), and thereby, a drilling process or a melt process on the workpiece can be performed in a short time. The laser processing apparatus 1 can control a time for melting the workpiece (melt time) and an area of the workpiece to be melted, because of selection (setting) of the processing condition (output condition of a laser beam) by the processing-condition setting unit 30. Further, the laser processing apparatus 1 can perform the drilling process or the melt process on a wide varieties of workpiece such as metal, plastic, and ceramics, because of selection of the processing condition by the processing-condition setting unit 30.

Figure 11:
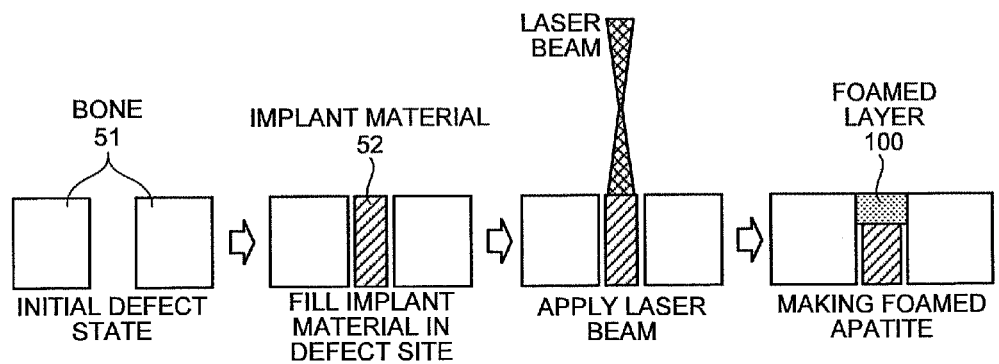
FIG. 11 is a schematic diagram for explaining a process for fabricating apatite by filling implant material in a defect site of bone.

Next, a method of fabricating the apatite 101 by the laser processing apparatus 1 is described below. FIG. 11 is a schematic diagram for explaining a process for fabricating apatite by filling implant material in a defect site of bone. First, apatite that is a non-foamed layer (the implant material 52 as the base material 200) is inserted in a defect site of the bone 51 in an initial defect state. Accordingly, the apatite (the implant material 52) is filled in the defect site of the bone 51.

Then, a laser beam is applied to the apatite (the implant material 52), so that foamed apatite is made on a top portion (a surface layer) of the implant material 52. The foamed apatite (the foamed layer 100) is filled in the defect site of the bone 51, and thereby, the apatite 101 is fabricated.

When a laser beam is applied to the implant material 52, the luminance detecting unit 41 of the laser processing apparatus 1 detects luminance of an area to be irradiated with the laser beam (the top surface of the implant material 52). The luminance detected by the luminance detecting unit 41 is sent to the processing-condition setting unit 30.

The processing-condition setting unit 30 selects a processing condition such as a laser beam, energy level, and a focal point depending on the type of the implant material 52 or the bone 51 (material or size) based on the luminance detected by the luminance detecting unit 41.

The processing-condition setting unit 30 can select a laser beam, energy level, and a focal point by using previously-set processing conditions. Further, the processing-condition setting unit 30 can set processing conditions of a workpiece based on a close contact state between the bone 51 and the foamed layer 100 or a required strength.

Further, when a laser beam is applied to the implant material 52, a melted area of the implant material 52 is more extended as a laser irradiation time is set longer. Therefore, it is applicable to change a time for laser irradiation depending on a size (an area of the top surface) of the implant material 52 that has been filled in the defect site. Moreover, the processing-condition setting unit 30 can set the laser irradiation time based on an instruction from a user.

The laser processing apparatus 1 starts processing on the implant material 52 by using the processing condition set by the processing-condition setting unit 30. The processing-condition setting unit 30 instructs laser irradiation on the workpiece (the implant material 52) for a predetermined time based on the laser irradiation time counted by the time counting unit 42 and the luminance detected by the luminance detecting unit 41. As a result, fabrication of the apatite 101 is completed.

In this manner, the processing-condition setting unit 30 sets the processing condition based on the luminance detected by the luminance detecting unit 41 and a time counted by the time counting unit 42, and then laser irradiation is performed. Therefore, laser irradiation suitable for a workpiece can be performed. As a result, the apatite 101 suitable for the workpiece (the bone 51 and the implant material 52) can be fabricated. Because luminance detected by the luminance detecting unit 41 changes when the implant material 52 is melted and the foamed layer 100 is made, it is applicable to change the processing condition depending on the change of the luminance.

When filling the non-foamed apatite (the implant material 52) that is in the solid state in the defect site of the bone 51, the size of the non-foamed apatite needs to be made smaller than the size of the defect site. Therefore, conventionally, even when the non-foamed apatite is filled in the bone 51, a space is remained between the non-foamed apatite and the bone 51, which makes it difficult to fix the non-foamed apatite to the bone 51.

According to the embodiment, a laser beam is applied to the non-foamed apatite after the non-foamed apatite is filled in the defect site of the bone 51, so that the bone 51 is burned due to heat that is used for melting the non-foamed apatite. Accordingly, the bone 51 produces gas that promotes generation of air bubbles, and thereby, the foamed layer 100 is made on the surface layer of the foamed apatite. Because the foamed layer 100 has an increased volume compared to that of the non-foamed apatite before laser irradiation, adhesiveness between the bone 51 and the foamed layer 100 increases, which is effective to fix the apatite (the non-foamed apatite and the foamed layer 100) into the defect site.

Figure 12:
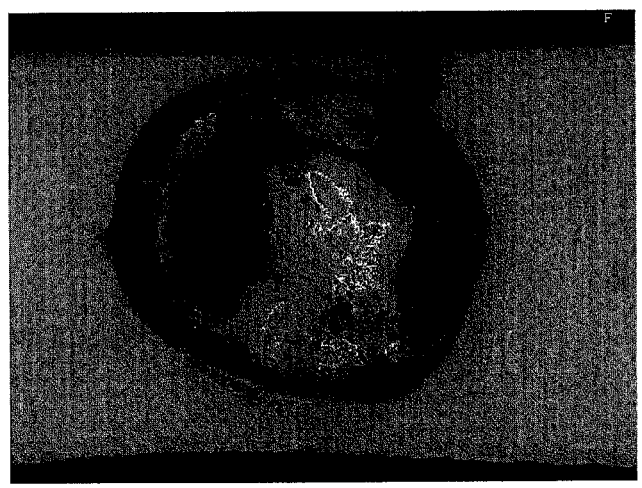
FIG. 12 is an image of the apatite fabricated through the process shown in FIG. 11.

FIG. 12 is an image of the apatite fabricated through the process shown in FIG. 11. Here, an example is shown in which the laser processing apparatus 1 has made the foamed apatite in the defect site of the bone 51.

The laser processing apparatus 1 can make the apatite 101 (forming the foamed layer 100) even for a missing tooth site. In this case, similar to the case of the bone 51, filling can be attained with high quality. The shape of the apatite to be inserted in the defect site of the bone 51 can be any shape such as granular, powder, or fractured pieces.

Figure 13:
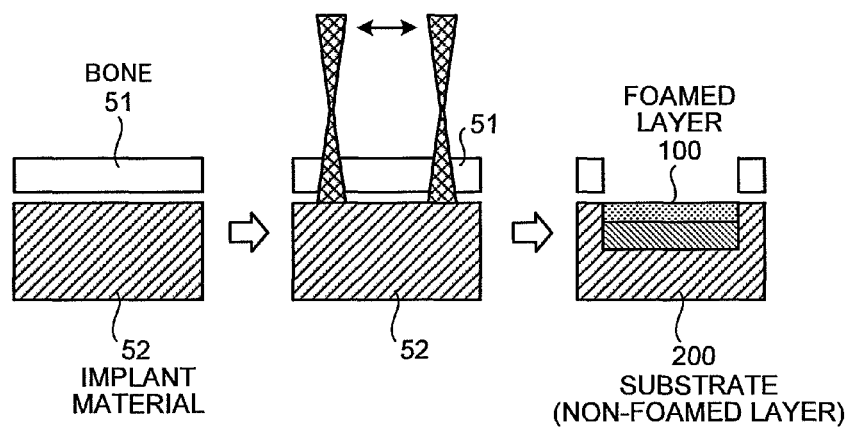
FIG. 13 is a schematic diagram for explaining a process for fabricating apatite by arranging bone on a top surface of implant material.

Next, a process for fabricating apatite by arranging the bone 51 on a top surface of the implant material 52 is described below. FIG. 13 is a schematic diagram for explaining a process for fabricating apatite by arranging the bone on a top surface of the implant material. Here, explanation is given below about a method of performing surface modification on the apatite by melting the surface layer of the apatite due to a heat source having high energy in a gas atmosphere produced by burned of the bone 51 with the heat source having high energy.

The bone 51 is arranged near a portion of the implant material 52 to be subjected to surface modification (the top surface of the implant material 52), and then the bone 51 is burned from a top surface side (the side opposite to the implant material 52) by being irradiated with a heat source having high energy, such as a laser beam. Accordingly, a hole is drilled in the bone 51 and then the implant material 52 is exposed. The surface of the apatite (the implant material 52) is melted by a heat source having high energy in a gas atmosphere produced by burning the bone 51. Accordingly, burned material of the bone 51 flows into a melt layer of the implant material 52, and thereby, the foamed layer 100 is made.

Because the foamed layer 100 is made only on a surface layer of a biomedical ceramics component (the apatite 101), less heat is conducted to the entire biomedical ceramics component. As a result, highly precise biomedical ceramics component can be obtained.

Figure 14:
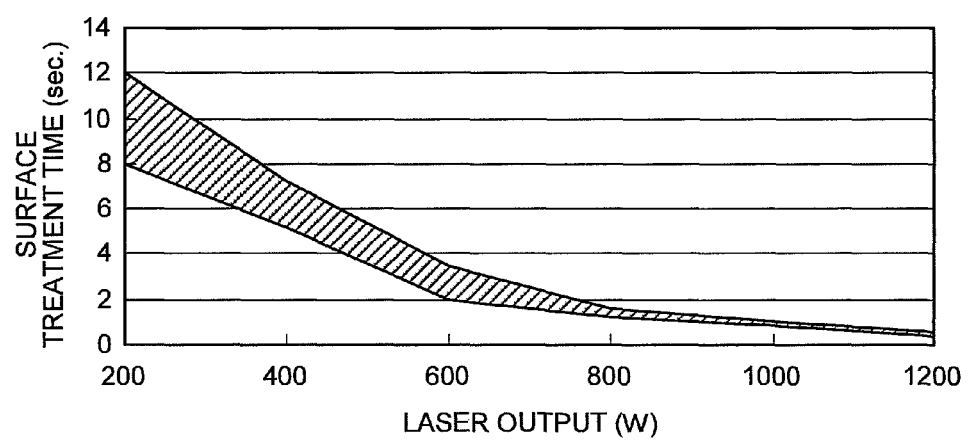
FIG. 14 is a schematic diagram illustrating an example of a processing condition for melting a surface layer of apatite.

Next, a processing condition for melting the surface layer of the apatite is described below. FIG. 14 is a schematic diagram illustrating an example of a processing condition for melting the surface layer of the apatite. Here, a processing condition in which the surface layer of the apatite is melted by 0.8 mm through processing using a $CO_2$ laser is illustrated as an example of the processing condition for melting the surface layer of the apatite.

As the laser output with respect to the surface layer of the apatite increases, the laser irradiation time for melting the surface layer of the apatite decreases. On the other hand, as the laser output with respect to the surface layer of the apatite decreases, variation in the laser irradiation time for melting the surface layer of the apatite increases.

Generally, when a temperature (baking temperature) for making foamed ceramics (the surface layer of the apatite) is low (e.g., 1000° C.), the base material 200 to be melted has high viscosity, resulting in forming air bubbles with decreased diameters. On the other hand, when a temperature for making foamed ceramics is high (e.g., 1300° C.), the base material 200 to be melted has low viscosity. As a result, formed air bubbles are associated with one another, resulting in forming air bubbles with increased diameters. The amount of the air bubbles contained in the foamed ceramics largely depends on a time for dispersion of the air bubbles. Specifically, as a time for melting the base material 200 increases, the amount of contained air bubbles increases.

When making the apatite 101 under a processing condition shown in FIG. 14, which illustrating a relation between the output amount of a laser beam and a laser irradiation time, the size of each air bubble increases as the output amount of the laser beam increases. Furthermore, as the laser irradiation time increases, the size of each air bubble increases, and the amount of contained air bubbles also increases.

When the size of each air bubble is in a range from 300 μm to 400 μm, infiltration characteristic with respect to cell (the bone 51) increases while strength decreases. Therefore, it is possible to make the apatite 101 by combining the foamed layers 100 of different types such that the size of each air bubble is made to be in a range from 300 μm to 400 μm in a portion of a contact surface between the apatite 101 and the bone 51 and the size of each air bubble in other portions is made to be 200 μm or smaller to maintain the strength of the contact surface. More particularly, the apatite 101 is made by changing a processing condition such that 200 $mm^2$ out of a contact area of 400 $mm^2$ between the bone 51 and the apatite 101 is processed by using a laser having output of 1000 W, and the remaining 200 $mm^2$ is processed by using a laser having output of 400 W.

The level of stress applied to an area between the bone 51 and the foamed layer 100 changes depending on a position of the bone 51 where a processed material (the apatite 101) is to be inserted and a type of the bone (e.g., age of a patient who is to have integration between the bone 51 and the apatite 101) where the processed material is to be inserted. Therefore, it is applicable to simulate an optimal area ratio of the foamed layers 100 of different types to be formed on the apatite 101, and determine a percentage of a processed area of the base material 200 depending on a processing condition, with respect to each integration process between the bone 51 and the foamed layer 100.

Meanwhile, when fabricating the apatite 101, luminance around a surface modified area is different in a case where a preferable surface modified layer (the surface layer of the implant material 52) is obtained on the apatite 101 and in a case where a preferable surface modified layer is not obtained (when less preferable integration with the bone 51 is performed). Therefore, if laser processing is performed without monitoring luminance, laser energy larger than the amount of heat necessary to be conducted for forming a foamed layer is applied to the implant material 52. As a result, an area to be subjected to thermal effects increases in a workpiece, and melted material of the implant material 52 cannot be coagulated while being dispersed, leading to worse surface modification on the apatite 101. On the other hand, in the laser processing apparatus 1 according to the embodiment, the luminance detecting unit 41 detects (monitors) luminance, and a processing condition is set based on the detected luminance. Therefore, a preferable surface modified area can be obtained.

Furthermore, because the apatite has relatively weak resistant to thermal shock, if the amount of heat to be conducted increases, crack may occur on the apatite. In the laser processing apparatus 1 according to the embodiment, because a processing condition is set based on luminance detected by the luminance detecting unit 41, a stable and preferable junction can be obtained.

While the laser processing apparatus 1 is configured to include the luminance detecting unit 41 and the time counting unit 42 in the embodiment, the configuration without the luminance detecting unit 41 and the time counting unit 42 can be applied. In this case, a user of the laser processing apparatus 1 detects a processing state of a workpiece by visual contact, and the processing-condition setting unit 30 sets a processing condition based on input of instruction information from the user. In other words, the laser processing apparatus 1 sets the processing condition for the workpiece without detection of the processing state by the luminance detecting unit 41 and the time counting unit 42.

In this manner, it is possible to obtain the apatite 101 having preferable cell infiltration characteristic. As a result, bone tissue and implant material (surgical implant material) that is biomaterial, such as ceramics or composite material, can be strongly integrated.

As described above, through continuous efforts, the inventors have succeeded in developing a technology for forming a foamed layer only on a surface layer made of molded apatite material. With this technology, it is possible to fabricate biological component made of apatite component to have two or more layered structure containing a foamed-layer and a non-foamed layer. Furthermore, it is possible to modify a portion of a non-foamed layer to be a foamed layer.

As a result, it is possible to design material having preferable affinity for biomedical tissue such that only a portion where cell infiltration needs to be improved is made into a foamed layer and a portion to which large stress is to be applied is made into a non-foamed layer.

In addition, by controlling energy for making a biological component, the size of each air bubble or the concentration of air bubbles in a foamed layer can be optimized depending on a use purpose of the biological component. Moreover, because the foamed layer of implant material is made in a gas atmosphere produced through vaporization of bone, bone component is remained inside the implant material and bone cell growth can be promoted. Accordingly, when bone and apatite are integrated, bone cell growth can be promoted. As a result, the bone and the apatite can be integrated instantly.

While, in the embodiment, new apatite (implant material) is made by using implant material made of apatite as substrate, it is possible to make new implant material by using implant material made of material other than apatite (plastic, ceramics, or the like) as substrate.

In this manner, according to the second embodiment, energy of a heat source, such as a laser beam, is applied to an area to be surface modified on the implant material 52. Therefore, it is possible to easily form the apatite 101 containing the foamed layer 100 on a portion of a non-foamed layer (the implant material 52). Accordingly, when the apatite 101 and bone are integrated, bone cell growth can be promoted by the foamed layer 100, so that an area of the non-foamed layer to which stress is applied can be strongly fixed. As a result, it is possible to obtain apatite that can integrate bone and implant material shortly and easily.

Furthermore, the processing-condition setting unit 30 sets a processing condition based on luminance detected by the luminance detecting unit 41 or a time counted by the time counting unit 42, and a laser is applied to a workpiece. Therefore, it is possible to appropriately perform laser irradiation and surface modification process depending on a workpiece.

INDUSTRIAL APPLICABILITY

As described above, the laser processing apparatus, the osseointegration method, the implant material, the implant-material fabrication method, and the implant-material fabricating apparatus of the present invention are suitable for integrating bone and implant material.

The invention claimed is:

1. A method of integrating bone and implant material, the method comprising:
   integrating the bone and the implant material by applying a laser beam to a junction of the bone and the implant material,
   wherein the integrating includes applying a laser beam to the junction such that the implant material is expanded by the application of the laser beam and expanded implant material fills a hole in the bone,
   melting the implant material by applying a laser beam to the implant material,
   foaming,
   wherein the foaming includes burning the bone by the application of the laser beam, and producing foamed air bubbles including bone component in melted implant material in a gas atmosphere obtained by burning the bone,
   and coagulating,
   wherein the coagulating includes forming a foamed layer on the implant material by stopping the application of the laser beam to the implant material such that the foamed air bubbles are confined and coagulated in the foamed layer.

2. The method according to claim 1, further comprising:
   drilling a hole in either one of the bone and the implant material in advance until the junction by applying a laser beam to either one of the bone and the implant material, wherein
   the integrating includes applying a laser beam to the junction via the hole drilled at the drilling.

3. The method according to claim 1, wherein the integrating includes applying a laser beam to the junction via a hole that is previously drilled in either one of the bone and the implant material.

4. The method according to claim 1, wherein the integrating includes
   detecting a processing state of at least one of the bone and the implant material,
   setting a processing condition for at least one of the bone and the implant material based on processing state detected at the detecting, and
   controlling an application of the laser beam based on the processing condition set at the setting.

5. The method according to claim 1, wherein the integrating includes
   bringing the bone and the implant material into tight contact with each other,
   setting a processing condition for at least one of the bone and the implant material based on at least one of a contact state between the bone and the implant material and a required strength when integrating the bone and the implant material, and controlling an application of the laser beam based on the processing condition set at the setting.

6. The method according to claim 1, wherein the integrating includes bringing the bone and the implant material into tight contact with each other, detecting a processing state of at least one of the bone and the implant material, setting a processing condition for at least one of the bone and the implant material based on at least one of a contact state between the bone and the implant material, a required strength, and the processing state detected at the detecting, and controlling an application of the laser beam based on the processing condition set at the setting.

7. The method according to claim 1, wherein the integrating includes inserting the implant material in a defect site of the bone, melting the implant material by applying a laser beam to the implant material inserted in the defect site of the bone.

8. The method according to claim 1, wherein the implant material is apatite.

* * * * *